(12) United States Patent
McCarthy

(10) Patent No.: US 8,951,565 B2
(45) Date of Patent: Feb. 10, 2015

(54) HEMOSTATIC COMPOSITIONS, ASSEMBLIES, SYSTEMS, AND METHODS EMPLOYING PARTICULATE HEMOSTATIC AGENTS FORMED FROM HYDROPHILIC POLYMER FOAM SUCH AS CHITOSAN

(71) Applicant: HemCon Medical Technologies, Inc., Portland, OR (US)

(72) Inventor: Simon J. McCarthy, Portland, OR (US)

(73) Assignee: HemCon Medical Technologies, Inc., Portland, OR (US)

( * ) Notice: Subject to any disclaimer, the term of this patent is extended or adjusted under 35 U.S.C. 154(b) by 0 days.

(21) Appl. No.: 14/255,297

(22) Filed: Apr. 17, 2014

(65) Prior Publication Data

US 2014/0228879 A1    Aug. 14, 2014

Related U.S. Application Data

(63) Continuation of application No. 11/485,886, filed on Jul. 13, 2006, now Pat. No. 8,741,335, which is a continuation-in-part of application No. 11/020,365, filed on Dec. 23, 2004, now abandoned, which is a continuation-in-part of application No. 10/480,827, filed on Oct. 6, 2004, now Pat. No. 7,482,503, which is a continuation-in-part of application No. 10/743,052, filed on Dec. 23, 2003, now Pat. No. 7,371,403.

(60) Provisional application No. 60/698,734, filed on Jul. 13, 2005.

(51) Int. Cl.
| | | |
|---|---|---|
| A61K 9/14 | (2006.01) | |
| A61K 9/50 | (2006.01) | |
| A01N 43/04 | (2006.01) | |
| C08B 37/08 | (2006.01) | |
| F26B 5/06 | (2006.01) | |
| F26B 5/14 | (2006.01) | |
| A61L 26/00 | (2006.01) | |
| A61L 15/28 | (2006.01) | |

(52) U.S. Cl.
CPC ............ *A61L 26/0023* (2013.01); *A61L 15/28* (2013.01); *A61L 26/0061* (2013.01); *A61L 2400/04* (2013.01)
USPC ............... 424/489; 424/499; 514/55; 514/62; 536/20; 34/284; 34/398

(58) Field of Classification Search
None
See application file for complete search history.

(56) References Cited

U.S. PATENT DOCUMENTS

| | | |
|---|---|---|
| 2,610,625 A | 9/1952 | Sifferd et al. |
| 2,858,830 A | 11/1958 | Robins |

(Continued)

FOREIGN PATENT DOCUMENTS

| | | |
|---|---|---|
| EP | 0353972 | 2/1990 |
| EP | 0477979 | 9/1991 |

(Continued)

OTHER PUBLICATIONS

Ohshima et al.; Eur. J. Plast Surg (1991) 14:207-211.*

(Continued)

*Primary Examiner* — Robert A Wax
*Assistant Examiner* — Jeffrey T Palenik
(74) *Attorney, Agent, or Firm* — Miller Nash Graham & Dunn LLP; Chandra E. Eidt

(57) ABSTRACT

Improved hemostatic agents take the form of granules or particles that can be used to stanch, seal, or stabilize a site of hemorrhage, including a noncompressible hemorrhage.

18 Claims, 5 Drawing Sheets

(56) References Cited

U.S. PATENT DOCUMENTS

| | | | |
|---|---|---|---|
| 2,923,664 A | 2/1960 | Cook et al. | |
| 3,551,556 A | 12/1970 | Kliment et al. | |
| 3,632,754 A | 1/1972 | Balassa | |
| 3,800,792 A | 4/1974 | McKnight et al. | |
| 3,801,675 A | 4/1974 | Russell | |
| 3,849,238 A | 11/1974 | Gould et al. | |
| 3,902,497 A | 9/1975 | Casey | |
| 3,911,116 A | 10/1975 | Balassa | |
| 3,954,493 A | 5/1976 | Battista et al. | |
| 3,977,406 A | 8/1976 | Roth | |
| 4,040,884 A | 8/1977 | Roth | |
| 4,056,103 A | 11/1977 | Kaczmarzyk et al. | |
| 4,068,757 A | 1/1978 | Casey | |
| 4,094,743 A | 6/1978 | Leuba | |
| 4,195,175 A | 3/1980 | Peniston et al. | |
| 4,292,972 A | 10/1981 | Palwelchak et al. | |
| 4,373,519 A | 2/1983 | Errede et al. | |
| 4,394,373 A | 7/1983 | Malette et al. | |
| 4,452,785 A | 6/1984 | Malette et al. | |
| 4,460,642 A | 7/1984 | Errede et al. | |
| 4,501,835 A | 2/1985 | Berke | |
| 4,524,064 A | 6/1985 | Nambu | |
| 4,532,134 A | 7/1985 | Malette et al. | |
| 4,533,326 A | 8/1985 | Anthony | |
| 4,541,426 A | 9/1985 | Webster | |
| 4,599,209 A * | 7/1986 | Dautzenberg et al. | 264/7 |
| 4,651,725 A * | 3/1987 | Kifune et al. | 602/49 |
| 4,684,370 A | 8/1987 | Barrett | |
| 4,699,135 A | 10/1987 | Motosugi et al. | |
| 4,759,348 A | 7/1988 | Cawood | |
| 4,772,419 A | 9/1988 | Malson et al. | |
| 4,833,237 A | 5/1989 | Kawamura et al. | |
| 4,948,540 A | 8/1990 | Nigam | |
| 4,952,618 A | 8/1990 | Olsen | |
| 4,956,350 A | 9/1990 | Mosbey | |
| 4,958,011 A | 9/1990 | Bade | |
| 4,960,413 A | 10/1990 | Sagar et al. | |
| 4,973,493 A | 11/1990 | Guire | |
| 4,977,892 A | 12/1990 | Ewall | |
| 5,006,071 A | 4/1991 | Carter | |
| 5,024,841 A | 6/1991 | Chu et al. | |
| 5,035,893 A | 7/1991 | Shioya et al. | |
| 5,062,418 A | 11/1991 | Dyer et al. | |
| 5,110,604 A | 5/1992 | Chu et al. | |
| 5,116,824 A | 5/1992 | Miyata et al. | |
| 5,154,928 A | 10/1992 | Andrews | |
| 5,206,028 A * | 4/1993 | Li | 424/484 |
| 5,254,301 A | 10/1993 | Sessions et al. | |
| 5,300,494 A | 4/1994 | Brode, II et al. | |
| 5,376,376 A | 12/1994 | Li | |
| 5,378,472 A | 1/1995 | Muzzarelli | |
| 5,420,197 A | 5/1995 | Lorenz et al. | |
| 5,454,719 A | 10/1995 | Hamblen | |
| 5,525,710 A | 6/1996 | Unger et al. | |
| 5,571,181 A | 11/1996 | Li | |
| 5,597,581 A | 1/1997 | Kaessmann et al. | |
| 5,643,596 A | 7/1997 | Pruss et al. | |
| 5,700,476 A | 12/1997 | Rosenthal et al. | |
| 5,738,860 A | 4/1998 | Schonfeldt | |
| 5,756,111 A | 5/1998 | Yoskikawa et al. | |
| 5,765,682 A | 6/1998 | Bley et al. | |
| 5,797,960 A | 8/1998 | Stevens et al. | |
| 5,821,271 A | 10/1998 | Roenigk | |
| 5,827,265 A | 10/1998 | Glinsky et al. | |
| 5,836,970 A * | 11/1998 | Pandit | 606/213 |
| 5,840,777 A | 11/1998 | Eagles et al. | |
| 5,858,292 A | 1/1999 | Dragoo et al. | |
| 5,858,350 A | 1/1999 | Vournakis et al. | |
| 5,952,618 A | 9/1999 | Deslauriers | |
| 5,961,478 A | 10/1999 | Timmermans | |
| 6,042,877 A | 3/2000 | Lyon et al. | |
| 6,054,122 A | 4/2000 | MacPhee et al. | |
| 6,103,369 A | 8/2000 | Lucast et al. | |
| 6,124,273 A | 9/2000 | Drohan et al. | |
| 6,156,330 A * | 12/2000 | Tsukada et al. | 424/408 |
| 6,162,241 A | 12/2000 | Coury et al. | |
| 6,225,521 B1 | 5/2001 | Gueret | |
| 6,270,515 B1 | 8/2001 | Linden et al. | |
| 6,406,712 B1 | 6/2002 | Rolf | |
| 6,448,462 B2 | 9/2002 | Groitzsch et al. | |
| 6,454,787 B1 | 9/2002 | Maddalo et al. | |
| 6,485,667 B1 | 11/2002 | Tan | |
| 6,486,285 B2 | 11/2002 | Fujita | |
| 6,548,081 B2 | 4/2003 | Sadozai et al. | |
| 6,548,569 B1 | 4/2003 | Williams et al. | |
| 6,552,244 B1 | 4/2003 | Jacques et al. | |
| 6,565,878 B2 | 5/2003 | Schoenfedlt et al. | |
| 6,566,577 B1 | 5/2003 | Addison et al. | |
| 6,599,891 B2 | 7/2003 | North et al. | |
| 6,693,180 B2 | 2/2004 | Lee et al. | |
| 6,726,712 B1 | 4/2004 | Raeder-Devens et al. | |
| 6,750,262 B1 | 6/2004 | Hähnle et al. | |
| 6,855,860 B2 | 2/2005 | Ruszczak et al. | |
| 6,863,924 B2 | 3/2005 | Ranganathan et al. | |
| 6,864,245 B2 | 3/2005 | Vournakis et al. | |
| 6,992,233 B2 | 1/2006 | Drake et al. | |
| 7,019,191 B2 | 3/2006 | Looney et al. | |
| 7,371,403 B2 * | 5/2008 | McCarthy et al. | 424/445 |
| 7,402,172 B2 | 7/2008 | Chin et al. | |
| 7,482,503 B2 * | 1/2009 | Gregory et al. | 602/48 |
| 7,546,812 B2 | 6/2009 | Eastin et al. | |
| 7,637,934 B2 | 12/2009 | Mangiardi et al. | |
| 7,671,102 B2 | 3/2010 | Gaserod et al. | |
| 7,820,872 B2 * | 10/2010 | Gregory et al. | 602/48 |
| 7,850,709 B2 | 12/2010 | Cummins et al. | |
| 7,897,832 B2 | 3/2011 | McAdams et al. | |
| 8,063,265 B2 | 11/2011 | Beck et al. | |
| 2001/0045177 A1 | 11/2001 | Harvey et al. | |
| 2002/0035391 A1 | 3/2002 | Mikus et al. | |
| 2002/0161376 A1 | 10/2002 | Barry et al. | |
| 2004/0243043 A1 * | 12/2004 | McCarthy et al. | 602/46 |
| 2005/0036955 A1 | 2/2005 | DeGould | |
| 2005/0123581 A1 | 6/2005 | Ringeisen et al. | |
| 2005/0137512 A1 | 6/2005 | Campbell et al. | |
| 2005/0143817 A1 | 6/2005 | Hunter et al. | |
| 2005/0147656 A1 | 7/2005 | McCarthy et al. | |
| 2005/0240137 A1 | 10/2005 | Zhu et al. | |
| 2006/0004314 A1 | 1/2006 | McCarthy et al. | |
| 2006/0008419 A1 | 1/2006 | Hissink et al. | |
| 2006/0083710 A1 | 4/2006 | Joerger et al. | |
| 2006/0184224 A1 | 8/2006 | Angel | |
| 2006/0211973 A1 | 9/2006 | Gregory et al. | |
| 2007/0021703 A1 | 1/2007 | McCarthy et al. | |
| 2007/0066920 A1 | 3/2007 | Hopman et al. | |
| 2007/0083137 A1 | 4/2007 | Hopman et al. | |
| 2007/0237811 A1 | 10/2007 | Scherr | |
| 2007/0255194 A1 | 11/2007 | Gudnason et al. | |
| 2007/0255243 A1 | 11/2007 | Kaun et al. | |
| 2007/0276308 A1 | 11/2007 | Huey et al. | |
| 2008/0132990 A1 | 6/2008 | Richardson | |
| 2008/0147019 A1 | 6/2008 | Song et al. | |
| 2008/0241229 A1 | 10/2008 | Li et al. | |
| 2011/0034410 A1 * | 2/2011 | McCarthy et al. | 514/55 |

FOREIGN PATENT DOCUMENTS

| | | |
|---|---|---|
| EP | 0643963 | 3/1995 |
| EP | 1462123 | 9/2004 |
| JP | 60-142927 | 7/1985 |
| JP | 62-039506 | 2/1987 |
| JP | 63-090507 | 4/1988 |
| JP | 07-116241 | 5/1995 |
| JP | 11-342153 | 12/1999 |
| JP | 2002-233542 | 8/2002 |
| WO | WO 95/05794 | 3/1995 |
| WO | WO 98/48861 | 11/1998 |
| WO | WO 99/02587 | 1/1999 |
| WO | WO 00/56256 | 9/2000 |
| WO | WO 02/102276 | 12/2002 |
| WO | WO 03/047643 | 6/2003 |
| WO | WO 03/079946 | 10/2003 |
| WO | WO 03/092756 | 11/2003 |
| WO | WO 03/101310 | 12/2003 |
| WO | WO 2004/047695 | 6/2004 |

(56) References Cited

FOREIGN PATENT DOCUMENTS

| WO | WO 2004/060412 | 7/2004 |
|---|---|---|
| WO | WO 2005/062880 | 7/2005 |
| WO | WO 2006/049463 | 5/2006 |
| WO | WO 2006/071649 | 7/2006 |
| WO | WO 2007/009050 | 1/2007 |
| WO | WO 2007/056066 | 5/2007 |
| WO | WO 2007/074327 | 7/2007 |
| WO | WO 2008/033462 | 3/2008 |
| WO | WO 2008/036225 | 3/2008 |

OTHER PUBLICATIONS

Percot et al.; Biomacromolecules (2003), 4, 12-18.*

Allan et al., "Biomedical Applications of Chitin and Chitosan." Chitin, Chitosan, and Related Enzymes—Accademic Press, Inc.: 119-133, 1984.

Anema et al., "Potential Uses of Absorbable Fibrin Adhesive Bandage for Genitourinary Trauma." World Journal of Surgery, vol. 25: 1573-1577, 2001.

Bégin et al., "Antimicrobial films produced from chitosan." International Journal of Biological Macromolecules, vol. 26: 63-67, 1999.

Belman et al., "From the Battlefield to the Street." Per declaration submitted in U.S. Appl. No. 10/480,827, dated Dec. 17, 2007, poster presentation was made at the ATACCC Conference, Aug. 2006.

Bendix., "Chemical synthesis of polyactide and its copolymers for medical applications." Polymer Degradation and Stability, vol. 59: 129-135, 1998.

Chan et al., "Comparision of Poly-N-acetyl Glucosamine (P-GlcNAc) with Absorbable Collagen (Actifoam), and Fibrin Sealant (Bolheal) for Achieving Hemostasis in a Swine Model of Splenic Hemorrhage." The Journal of Trauma: 454-458, 2000.

CNN Transcript—3pp., Jun. 8, 2006.

Cole et al., "A pilot study evaluating the efficacy of a fully acetylated poly-N-acetyl glucosamine membrane formulation as a topical hemostatic agent." Surgery, vol. 126, No. 3: 510-517, 1999.

HemCon Manufacturing Materials. Per declaration submitted in U.S. Appl. No. 10/480,827, dated Dec. 17, 2007, materials were submitted as supporting evidence for declaration.

Horesh et al., "Pre-hospital use of the HemCon bandage." Per declaration submitted in U.S. Appl. No. 10/480,827, dated Dec. 17, 2007, poster presentation was made at the WCDEM Conference, May 2007.

Kiley, Kevin, "Department of the Army memo." Jul. 20, 2005.

Kumar, Ravi, "Chitin and chitosan fibres: A review." Bulletin of Material Science: vol. 22, No. 5: 905-915, Aug. 1999.

Luo et al., "The role of poly(ethylene glycol) in the formation of silver nanoparticles." Journal of Colloid and Interface Science, vol. 288: 444-448, 2005.

Malette et al., "Chitosan: A New Hemostatic." The Annals of Thoratic Surgery, vol. 36, No. 1: 55-58, Jul. 1983.

Martin et al., "Medical applications of poly-4-hydroxybutyrate: a strong flexible absorbable biomaterial." Biochemical Engineering Journal, vol. 16: 97-105, 2003.

Mi et al., "Fabrication and characterization of a sponge-like asymmetric chitosan membrane as a wound dressing." Biomaterials, vol. 22: 165-173, 2001.

Moody, Robin J., "HemCon bandage stakes claim to soldier's kit bag." Portland Business Journal, Nov. 4, 2005.

Ohshima et al., "Clinical Application of Chitin Non-Woven Fabric as Wound Dressing." European Journal of Plastic Surgery, vol. 10: 66-69, 1987.

Ohshima et al., "Clinical application of new chitin non-woven fabric and new chitin sponge sheet as wound dressing." European Journal of Plastic Surgery, vol. 14: 207-211, 1991.

Olsen et al., "Biomedical Applications of Chitin and its Derivatives." Chitin and Chitosan: Proceedings from the 4th International Conference on Chitin and Chitosan, 813-829, 1988.

Park et al., "Platelet derived growth factor releasing chitosan sponge for periodontal bone regeneration." Biomaterials, vol. 21: 153-159, 2000.

Percot et al., "Optimization of Chitin Extraction from Shrimp Shells." Biomacromolecules, vol. 4: 12-18, 2003.

Pusateri et al., "Advanced Hemostatic Dressing Development Program: Animal Model Selection Criteria and Results of a Study of Nine Hemostatic Dressings in a Model of Severe Large Venous Hemorrhage and Hepatic Injury in Swine." The Journal of Trauma, vol. 55: 518-526, 2003.

Sandford, Paul A., "Chitosan: Commercial Uses and Potential Applications." Chitin and Chitosan: Proceedings from the 4th International Conference on Chitin and Chitosan, 51-69, 1988.

Sandford et al., "Biomedical Applications of High-Purity Chitosan." Water-Soluble Polymers: Chapter 28: 430-445, 1991.

Sandford, Paul A., "Biomedical Applications of New Forms of Chitin/Chitosan." Chitin Derivatives in Life Science, 12pp., 1992.

Schoof et al., "Control of Pore Structure and Size in Freeze-Dried Collagen Sponges." Journal of Biomedical Material Research, vol. 58: 352-357, 2001.

Siekman, Philip, "A Shrimp Bandage?" Fortune Small Business, pp. 67-68, 2006.

Sondeen et al., "Comparison of 10 Different Hemostatic Dressings in an Aortic Injury." The Journal of Trauma, vol. 54, No. 2: 280-285, 2003.

Wedmore et al., "A Special Report on the Chitosan-based Hemostatic Dressing: Experience in Current Combat Operations." The Journal of Trauma, vol. 60: 655-658, 2006.

Wilson, J.R., "The Army's Greatest Inventions." U.S. Army Materiel Command, pp. 30-37, 2005.

Wu et al., "Development of In Vitro Adhesion Test for Chitosan Bandages." Society for Biomaterials 30th Annual Meeting Transactions, 2005, 1pg.

Database WPI, Week 200873 Thomson Scientific, London GB, AN 2008-M34232, XP002695569 & CN 101138648, Mar. 12, 2008.

* cited by examiner

US 8,951,565 B2

HEMOSTATIC COMPOSITIONS, ASSEMBLIES, SYSTEMS, AND METHODS EMPLOYING PARTICULATE HEMOSTATIC AGENTS FORMED FROM HYDROPHILIC POLYMER FOAM SUCH AS CHITOSAN

RELATED APPLICATIONS

This application is a continuation of U.S. patent application Ser. No. 11/485,886 filed on Jul. 13, 2006, entitled "Hemostatic Compositions, Assemblies, Systems, And Methods Employing Particulate Hemostatic Agents Formed From Hydrophilic Polymer Foam Such As Chitosan"; which is a continuation in part of U.S. patent application Ser. No. 11/020,365 filed on Dec. 23, 2004, entitled "Tissue Dressing Assemblies, Systems, and Methods Formed From Hydrophilic Polymer Sponge Structures Such as Chitosan"; which is a continuation in part of U.S. patent application Ser. No. 10/743,052, filed on Dec. 23, 2003, entitled "Wound Dressing and Method of Controlling Severe Life-Threatening Bleeding"; which is a continuation in part of U.S. patent application Ser. No. 10/480,827, filed on Oct. 6, 2004, entitled "Wound Dressing and Method of Controlling Severe Life-Threatening Bleeding," which was a national stage filing under 37 C.F.R. §371 of International Application No. PCT/U502/18757, filed on Jun. 14, 2002, which are each incorporated herein by reference. U.S. patent application Ser. No. 11/485,886 also claims the benefit of U.S. Provisional Application Ser. No. 60/698,734, filed Jul. 13, 2005, and entitled "Hemostatic Compositions, Assemblies, Systems, and Methods Employing Particulate Hemostatic Agents Formed from Hydrophilic Polymer Foam Such As Chitosan, which is incorporated herein by reference.

FIELD OF THE INVENTION

The invention is generally directed to agents applied externally or internally on a site of tissue injury or tissue trauma to ameliorate bleeding, fluid seepage or weeping, or other forms of fluid loss.

BACKGROUND OF THE INVENTION

Hemorrhage is the leading cause of death from battlefield trauma and the second leading cause of death after trauma in the civilian community. Non-compressible hemorrhage (hemorrhage not readily accessible to direct pressure, such as intracavity bleeding) contributes to the majority of early trauma deaths. Apart from proposals to apply a liquid hemostatic foam and recombinant factor VIIa to the non-compressible bleeding sites, very little has been done to address this problem. There is a critical need to provide more effective treatment options to the combat medic for controlling severe internal hemorrhage such as intracavity bleeding.

Control of intracavity bleeding is complicated by many factors, chief among which are: lack of accessibility by conventional methods of hemostatic control such as application of pressure and topical dressings; difficulty in assessing the extent and location of injury; bowel perforation, and interferences caused by blood flow and pooling of bodily fluids.

SUMMARY OF THE INVENTION

The invention provides improved hemostatic agents that can be used to stanch, seal, or stabilize a site of hemorrhage, including a noncompressible hemorrhage, such as at a site of intracavity bleeding. The invention provides rapid delivery of a safe and effective hemostatic agent to a general site of bleeding; enhanced promotion of strong clot formation at the site of bleeding; and ability (if necessary) to apply tamponade over the field of injury. The invention also provides an enhanced rate of wound healing with reduced fibrotic adhesion and reduced opportunity for wound infection. The invention therefore addresses many of the significant issues related to current difficulties in controlling hemorrhage including intracavitary hemorrhage and recovery from these types of injury.

One aspect of the invention provides a hemostatic agent that can be applied to a site of bleeding to stanch, seal, or stabilize the site, with our without the application of direct pressure or compression.

One aspect of the invention provides a hemostatic agent that takes the form of a granule or particle that can be applied to stanch, seal, or stabilize a hemorrhage, with our without the application of direct pressure or compression.

One aspect of the invention provides a chitosan material in the form of a granule or particle that can be applied to stanch, seal, or stabilize a hemorrhage, with our without the application of direct pressure or compression.

One aspect of the invention provides a densified chitosan material in the form of a granule or particle that can be applied to stanch, seal, or stabilize a hemorrhage, with our without the application of direct pressure or compression.

One aspect of the invention provides a hemostatic agent matrix in the form of a granule or particle that carries within it dense chitosan beads.

One aspect of the invention provides a hemostatic agent matrix in the form of a granule or particle that carries within it a polymer mesh material.

One aspect of the invention provides a composite of a hemostatic agent that takes the form of a granule or particle interspersed with strips of pieces of a polymer mesh material that can be applied together to stanch, seal, or stabilize a hemorrhage, with our without the application of direct pressure or compression.

One aspect of the invention provides a hemostatic agent that takes the form of a granule or particle that can be applied within a polymer mesh socklet to stanch, seal, or stabilize a hemorrhage, with our without the application of direct pressure or compression.

One aspect of the invention provides a chitosan material in the form of a granule or particle that carries within it dense chitosan beads.

One aspect of the invention provides a chitosan material in the form of a granule or particle that carries within it a polymer mesh material.

One aspect of the invention provides a composite of a chitosan material that takes the form of a granule or particle interspersed with strips of pieces of a polymer mesh material that can be applied together to stanch, seal, or stabilize a hemorrhage, with our without the application of direct pressure or compression.

One aspect of the invention provides a hemostatic agent that takes the form of a granule or particle that can be applied within a polymer mesh socklet to stanch, seal, or stabilize a hemorrhage, with our without the application of direct pressure or compression.

One aspect of the invention provides methods of treat bleeding using the materials having the technical features described.

One aspect of the invention provides methods of treat intracavity bleeding using the materials having the technical features described.

One aspect of the invention provides a granular hemostatic material that is obtained from controlled grinding of deproteinized, and optionally also fully or partially decalcified, crustacean shell material, which is then partially (30%) or near fully (80-85%) deacetylized.

Other features and advantages of the invention shall be apparent based upon the accompanying description, drawings, and listing of key technical features.

DESCRIPTION OF THE DRAWINGS

FIG. 12 is an alternative way of delivering a bolus of the granules or particles shown in FIG. 2 or 4 or 7 to an injury site without use of a containment socklet or the like.

DETAILED DESCRIPTION

Although the disclosure hereof is detailed and exact to enable those skilled in the art to practice the invention, the physical embodiments herein disclosed merely exemplify the invention, which may be embodied in other specific structure. While the preferred embodiment has been described, the details may be changed without departing from the invention, which is defined by the claims. For the purpose of illustration, the invention is disclosed in the context of treating a noncompressible hemorrhage. It should be appreciated that the invention is generally capable of treating any hemorrhage, with or without the application of pressure.

I. HEMOSTATIC AGENT

A. Overview

Figure 1A:
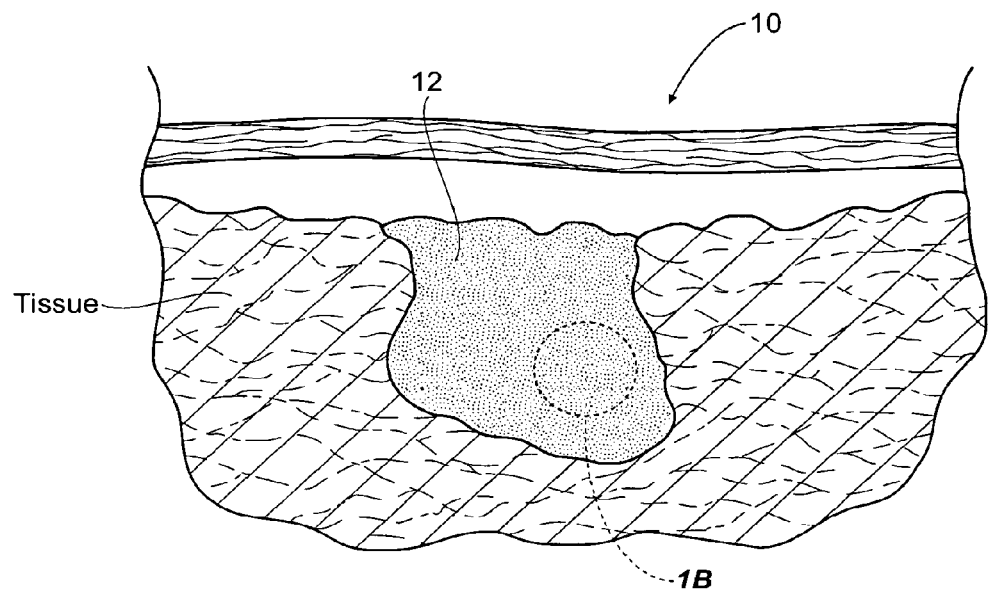
FIG. 1A is a schematic anatomic view of an intracavity site of noncompressible hemorrhage, into which a hemostatic agent has been applied to stanch, seal, or stabilize the site.

FIG. 1A shows a site 10 of an intracavity abdominal injury, where severe internal bleeding will occur if steps are not taken to stanch, seal, or stabilize the site. The site 10 is the location of a noncompressible hemorrhage, meaning that the hemorrhage is not readily accessible to direct pressure.

Figure 1B:
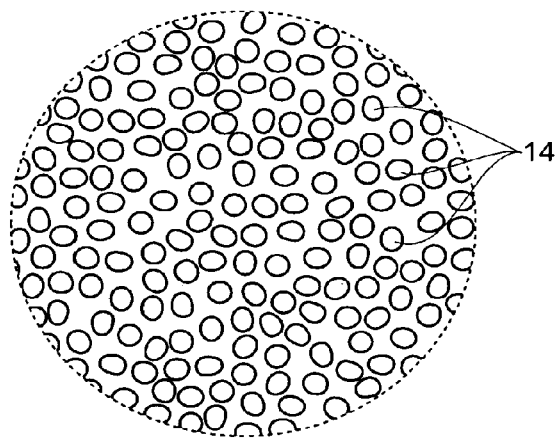
FIG. 1B is an enlarged view of the hemostatic agent shown in FIG. 1A, showing the granules or particles that comprise the agent.

As shown in FIGS. 1A and 1B, a hemostatic agent 12 that embodies the features of the invention has been applied to stanch, seal, or stabilize the site 10 without the application of direct pressure or compression. The agent 12 takes the form of discrete particles 14 of a biodegradable hydrophilic polymer (best shown in FIG. 1B and FIG. 2).

The polymer of which the particles 14 are formed has been selected to include a biocompatible material that reacts in the presence of blood, body fluid, or moisture to become a strong adhesive or glue. Desirably, the polymer from which the particles 14 are formed also desirably possess other beneficial attributes, for example, anti-bacterial and/or anti-microbial anti-viral characteristics, and/or characteristics that accelerate or otherwise enhance the body's defensive reaction to injury. The polymer material comprising the particles 14 has desirably been densified or otherwise treated to make the particles 14 resistant to dispersal away from the site 10 by flowing blood and/or other dynamic conditions affecting the site 10.

The agent 12 thereby serves to stanch, seal, and/or stabilize the site 10 against bleeding, fluid seepage or weeping, or other forms of fluid loss. The agent 12 also desirably forms an anti-bacterial and/or anti-microbial and/or anti-viral protective barrier at or surrounding the tissue treatment site 10. The agent 12 can applied as temporary intervention to stanch, seal, and/or stabilize the site 10 on an acute basis. The agent 12 can also be augmented, as will be described later, to make possible more permanent internal use.

B. The Hemostatic Particles

Figure 2:
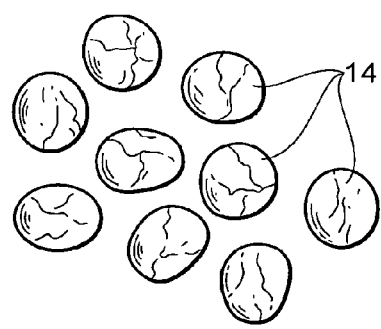
FIG. 2 is a further enlarged view of the granules or particles shown in FIG. 1B.

The particles 14 shown in FIG. 2 may comprise a hydrophilic polymer form, such as a polyacrylate, an alginate, chitosan, a hydrophilic polyamine, a chitosan derivative, polylysine, polyethylene imine, xanthan, carrageenan, quaternary ammonium polymer, chondroitin sulfate, a starch, a modified cellulosic polymer, a dextran, hyaluronan or combinations thereof. The starch may be of amylase, amylopectin and a combination of amylopectin and amylase.

In a preferred embodiment, the biocompatible material of the particles 14 comprises a non-mammalian material, which is most preferably poly[β-(1→4)-2-amino-2-deoxy-D-glucopyranose, which is more commonly referred to as chitosan. The chitosan selected for the particles 14 preferably has a weight average molecular weight of at least about 100 kDa, and more preferably, of at least about 150 kDa. Most preferably, the chitosan has a weight average molecular weight of at least about 300 kDa.

In forming the particles 14, the chitosan is desirably placed into solution with an acid, such as glutamic acid, lactic acid, formic acid, hydrochloric acid and/or acetic acid. Among these, hydrochloric acid and acetic acid are most preferred, because chitosan acetate salt and chitosan chloride salt resist dissolution in blood, whereas chitosan lactate salt and chitosan glutamate salt do not. Larger molecular weight (Mw) anions disrupt the para-crystalline structure of the chitosan salt, causing a plasticization effect in the structure (enhanced flexibility). Undesirably, they also provide for rapid dissolution of these larger Mw anion salts in blood.

One preferred form of the particles 14 comprises an "uncompressed" chitosan acetate matrix of density less than 0.035 g/cm$^3$ that has been formed by freezing and lyophilizing a chitosan acetate solution, which is then densified by compression to a density of from 0.6 to 0.5 g/cm$^3$, with a most preferred density of about 0.25 to 0.5 g/cm³. This chitosan matrix can also be characterized as a compressed, hydrophilic sponge structure. The densified chitosan matrix exhibits all of the above-described characteristics deemed to be desirable. It also possesses certain structural and mechanical benefits that lend robustness and longevity to the matrix during use, as will be described in greater detail later.

After formation in the manner just described, the sponge structure is granulated, e.g., by a mechanical process, to a desired particle diameter, e.g., at or near 0.9 mm.

The chitosan matrix from which the particles 14 are formed presents a robust, permeable, high specific surface area, positively charged surface. The positively charged surface creates a highly reactive surface for red blood cell and platelet interaction. Red blood cell membranes are negatively charged, and they are attracted to the chitosan matrix. The cellular membranes fuse to chitosan matrix upon contact. A clot can be formed very quickly, circumventing immediate need for clotting proteins that are normally required for hemostasis. For this reason, the chitosan matrix is effective for both normal as well as anti-coagulated individuals, and as well as persons having a coagulation disorder like hemophilia. The chitosan matrix also binds bacteria, endotoxins, and microbes, and can kill bacteria, microbes, and/or viral agents on contact. Furthermore, chitosan is biodegradable within the body and is broken down into glucosamine, a benign substance.

C. Manufacture of the Hemostatic Particles

A desirable methodology for making the particles 14 will now be described. This methodology is shown schematically in FIG. 3. It should be realized, of course, that other methodologies can be used.

1. Preparation of a Chitosan Solution

The chitosan used to prepare the chitosan solution preferably has a fractional degree of deacetylation greater than 0.78 but less than 0.97. Most preferably the chitosan has a fractional degree of deacetylation greater than 0.85 but less than 0.95. Preferably the chitosan selected for processing into the matrix has a viscosity at 25° C. in a 1%(w/w) solution of 1%(w/w) acetic acid (AA) with spindle LVI at 30 rpm, which is about 100 centipoise to about 2000 centipoise. More preferably, the chitosan has viscosity at 25° C. in a 1%(w/w) solution of 1%(w/w) acetic acid (AA) with spindle LVI at 30 rpm, which is about 125 centipoise to about 1000 centipoise. Most preferably, the chitosan has viscosity at 25° C. in a 1%(w/w) solution of 1%(w/w) acetic acid (AA) with spindle LV1 at 30 rpm, which is about 400 centipoise to about 800 centipoise.

The chitosan solution is preferably prepared at 25° C. by addition of water to solid chitosan flake or powder and the solid dispersed in the liquid by agitation, stirring or shaking. On dispersion of the chitosan in the liquid, the acid component is added and mixed through the dispersion to cause dissolution of the chitosan solid. The rate of dissolution will depend on the temperature of the solution, the molecular weight of the chitosan and the level of agitation. Preferably the dissolution step is performed within a closed tank reactor with agitating blades or a closed rotating vessel. This ensures homogeneous dissolution of the chitosan and no opportunity for high viscosity residue to be trapped on the side of the vessel. Preferably the chitosan solution percentage (w/w) is greater than 0.5% chitosan and less than 2.7% chitosan. More preferably the chitosan solution percentage (w/w) is greater than 1% chitosan and less than 2.3% chitosan. Most preferably the chitosan solution percentage is greater than 1.5% chitosan and less than 2.1% chitosan. Preferably the acid used is acetic acid. Preferably the acetic acid is added to the solution to provide for an acetic acid solution percentage (w/w) at more than 0.8% and less than 4%. More preferably the acetic acid is added to the solution to provide for an acetic acid solution percentage (w/w) at more than 1.5% (w/w) and less than 2.5%.

The structure or form producing steps for the chitosan matrix are typically carried out from solution and can be accomplished employing techniques such as freezing (to cause phase separation), non-solvent die extrusion (to produce a filament), electro-spinning (to produce a filament), phase inversion and precipitation with a non-solvent (as is typically used to produce dialysis and filter membranes) or solution coating onto a preformed sponge-like or woven product. In the case of freezing, where two or more distinct phases are formed by freezing (typically water freezing into ice with differentiation of the chitosan biomaterial into a separate solid phase), another step is required to remove the frozen solvent (typically ice), and hence produce the chitosan matrix 12 without disturbing the frozen structure. This may be accomplished by a freeze-drying and/or a freeze substitution step. The filament can be formed into a non-woven sponge-like mesh by non-woven spinning processes. Alternately, the filament may be produced into a felted weave by conventional spinning and weaving processes. Other processes that may be used to make the biomaterial sponge-like product include dissolution of added porogens from a solid chitosan matrix or boring of material from said matrix.

2. Degassing the Aqueous Chitosan Solution

Preferably (see FIG. 3, Step B), the chitosan biomaterial 16 is degassed of general atmospheric gases. Typically, degassing is removing sufficient residual gas from the chitosan biomaterial so that, on undergoing a subsequent freezing operation, the gas does not escape and form unwanted large voids or large trapped gas bubbles in the subject wound dressing product. The degassing step may be performed by heating a chitosan biomaterial, typically in the form of a solution, and then applying a vacuum thereto. For example, degassing can be performed by heating a chitosan solution to about 45° C. immediately prior to applying vacuum at about 500 mTorr for about 5 minutes while agitating the solution.

In one embodiment, certain gases can be added back into the solution to controlled partial pressures after initial degassing. Such gases would include but are not limited to argon, nitrogen and helium. An advantage of this step is that solutions containing partial pressures of these gases form microvoids on freezing. The microvoid is then carried through the sponge as the ice-front advances. This leaves a well-defined and controlled channel that aids sponge pore interconnectivity.

3. Freezing the Aqueous Chitosan Solution

Next (see FIG. 3, Step C), the chitosan biomaterial 16—which is typically now in acid solution and degassed, as described above—is subjected to a freezing step. Freezing is preferably carried out by cooling the chitosan biomaterial solution supported within a mold and lowering the solution temperature from room temperature to a final temperature below the freezing point. More preferably this freezing step is performed on a plate freezer whereby a thermal gradient is introduced through the chitosan solution in the mold by loss of heat through the plate cooling surface. Preferably this plate cooling surface is in good thermal contact with the mold. Preferably the temperature of the chitosan solution and mold before contact with the plate freezer surface are near room temperature. Preferably the plate freezer surface temperature is not more than −10° C. before introduction of the mold+solution. Preferably the thermal mass of the mold+solution is less than the thermal mass of the plate freezer shelf+heat transfer fluid. Preferably the molds are formed from, but are not limited to, a metallic element such as iron, nickel, silver, copper, aluminum, aluminum alloy, titanium, titanium alloy, vanadium, molybdenum, gold, rhodium, palladium, platinum and/or combinations thereof. The molds may also be coated with thin, inert metallic coatings such as titanium, chromium, tungsten, vanadium, nickel, molybdenum, gold and platinum in order to ensure there is no reaction with the acid component of the chitosan solution and the chitosan salt matrix. Thermally insulating coatings or elements may be used in conjunction with the metallic molds to control heat transfer in the molds. Preferably the mold surfaces do not bind with the frozen chitosan solution. The inside surface of the mold is preferably coated with a thin, permanently-bound, fluorinated release coating formed from polytetrafluoroethylene (Teflon), fluorinated ethylene polymer (FEP), or other fluorinated polymeric materials. Although coated metallic molds are preferable, thin walled plastic molds can be a convenient alternative for supporting the solution. Such plastic molds would include, but not be limited to, molds prepared by injection molding, machining or thermoforming from polyvinylchloride, polystyrene, acrylonitrile-butadiene-styrene copolymers, polyesters, polyamides, polyurethanes and polyolefins. An advantage of the metallic molds combined with local placement of thermally insulating elements is that they also provide opportunity for improved control of heat flow and structure within the freezing sponge. This improvement in heat flow control results from large thermal conductivity differences between thermally conducting and thermally insulating element placements in the mold.

Freezing of the chitosan solution in this way enables the preferred structure of the agent 12 to be prepared.

The plate freezing temperature affects the structure and mechanical properties of the final chitosan matrix 16. The plate freezing temperature is preferably not higher than about −10° C., more preferably not more than about −20° C., and most preferably not more than about −30° C. When frozen at −10° C., the structure of the uncompressed chitosan matrix 16 is very open and vertical throughout the open sponge structure. When frozen at −25° C., the structure of the uncompressed chitosan matrix 12 is more closed, but it is still vertical. When frozen at −40° C., the structure of the uncompressed chitosan matrix 16 is closed and not vertical. Instead, the chitosan matrix 16 comprises more of a reinforced, inter-meshed structure. The adhesive/cohesive sealing properties of the chitosan matrix 16 are observed to improve as lower freezing temperatures are used. A freezing temperatures of about −40° C. forms a structure for the chitosan matrix 16 having superior adhesive/cohesive properties.

During the freezing step, the temperature may be lowered over a predetermined time period. For example, the freezing temperature of a chitosan biomaterial solution may be lowered from room temperature to −45° C. by plate cooling application of a constant temperature cooling ramp of between about −0.4° C./mm to about −0.8° C./mm for a period of about 90 minutes to about 160 minutes.

4. Freeze Drying the Chitosan/Ice Matrix

Figure 3:
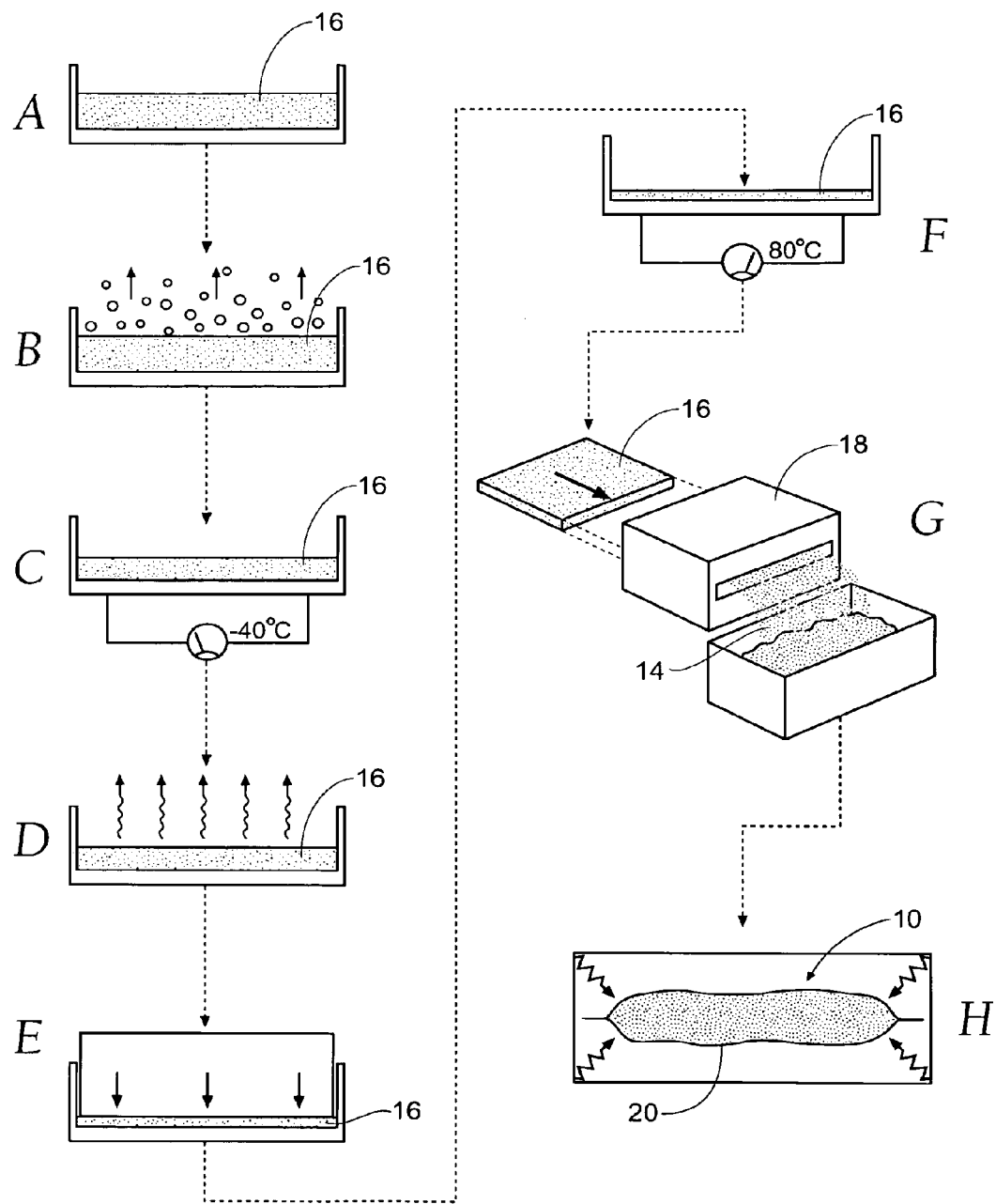
FIG. 3 is a schematic flow chart view of a process of manufacturing the granules or particles shown in FIG. 2 from a chitosan material.

The frozen chitosan/ice matrix desirably undergoes water removal from within the interstices of the frozen material (see FIG. 3, Step D). This water removal step may be achieved without damaging the structural integrity of the frozen chitosan biomaterial. This may be achieved without producing a liquid phase, which can disrupt the structural arrangement of the ultimate chitosan matrix 16. Thus, the ice in the frozen chitosan biomaterial passes from a solid frozen phase into a gas phase (sublimation) without the formation of an intermediate liquid phase. The sublimated gas is trapped as ice in an evacuated condenser chamber at substantially lower temperature than the frozen chitosan biomaterial.

The preferred manner of implementing the water removal step is by freeze-drying, or lyophilization. Freeze-drying of the frozen chitosan biomaterial can be conducted by further cooling the frozen chitosan biomaterial. Typically, a vacuum is then applied. Next, the evacuated frozen chitosan material may be gradually heated.

More specifically, the frozen chitosan biomaterial may be subjected to subsequent freezing preferably at about −15° C., more preferably at about −25° C., and most preferably at about −45° C., for a preferred time period of at least about 1 hour, more preferably at least about 2 hour, and most preferably at least about 3 hour. This step can be followed by cooling of the condenser to a temperature of less than about −45° C., more preferably at about −60° C., and most preferably at about −85° C. Next, a vacuum in the amount of preferably at most about 100 mTorr, more preferably at most about 150 mTorr, and most preferably at least about 200 mTorr, can be applied. The evacuated frozen chitosan material can be heated preferably at about −25° C., more preferably at about −15° C., and most preferably at about −10° C., for a preferred time period of at least about 1 hour, more preferably at least about 5 hour, and most preferably at least about 10 hour.

Further freeze drying, maintaining vacuum pressure at near 200 mTorr, is conducted at a shelf temperature of about 20° C., more preferably at about 15° C., and most preferably at about 10° C., for a preferred time period of at least about 36 hours, more preferably at least about 42 hours, and most preferably at least about 48 hours.

5. Densification of the Chitosan Matrix

The chitosan matrix 16 before densification (density near 0.03 g/cm') will be called an "uncompressed chitosan matrix." This uncompressed matrix is ineffective in stanching bleeding since it rapidly dissolves in blood and has poor mechanical properties. The chitosan biomaterial is necessarily compressed (see FIG. 3, Step E). Compression loading normal to the hydrophilic matrix polymer surface with heated platens can be used to compress the dry "uncompressed" chitosan matrix 16 to reduce the thickness and increase the density of the matrix. The compression step, which will sometimes be called in shorthand "densification," significantly increases adhesion strength, cohesion strength and dissolution resistance of the chitosan matrix 12. Appropriately frozen chitosan matrices 16 compressed above a threshold density (close to 0.1 g/cm3) do not readily dissolve in flowing blood at 37° C.

The compression temperature is preferably not less than about 60° C., more preferably it is not less than about 75° C. and not more than about 85° C.

The densified chitosan biomaterial is next preferably preconditioned by heating chitosan matrix 16 in an oven to a temperature of preferably up to about 75° C., more preferably to a temperature of up to about 80° C., and most preferably to a temperature of preferably up to about 85° C. (FIG. 3, Step F). Preconditioning is typically conducted for a period of time up to about 0.25 hours, preferably up to about 0.35 hours, more preferably up to about 0.45 hours, and most preferably up to about 0.50 hours. This pre-conditioning step provides further significant improvement in dissolution resistance with a small cost in a 20-30% loss of adhesion properties.

A backing may be secured to one side of the chitosan matrix 16 to facilitate further handling. The backing can be attached or bonded by direct adhesion with a top layer of chitosan matrix 16. Alternatively, an adhesive such as 3M 9942 Acrylate Skin Adhesive, or fibrin glue, or cyanoacrylate glue can be employed.

6. Granulation of the Densified Chitosan Matrix

Matrix 16 is granulated, e.g., by a mechanical process to a desired particle diameter, e.g., at or near about 0.9 mm. Simple mechanical granulation of the chitosan matrix 16 through a suitable mechanical device 18 (as shown in FIG. 3, Step G) can be used to prepare chitosan sponge particles 14 of close to 0.9 mm in diameter. Other granulation methodologies can be used. For example, off the shelf stainless steel grinding/granulating laboratory/food processing equipment can be used. More robust, purpose designed, and more process-controlled systems can also be used.

Granulation of the chitosan matrix 16 can be conducted under ambient temperature or liquid nitrogen temperature conditions.

Preferably, a well-defined particle size distribution of particle granulate is prepared. The particle size distribution can be characterized using, e.g., Leica ZP6 APO stereomicroscope and Image Analysis MC software.

7. Sterilization

The desired weight volume of particles 14 can be subsequently packaged in a pouch 20, which is desirably purged with an inert gas such as either argon or nitrogen gas, evacuated and heat sealed. The pouch 20 acts to maintain interior contents sterility over an extend time (at least 24 months) and also provides a very high barrier to moisture and atmospheric gas infiltration over the same period.

After pouching, the particles 14 are desirably subjected to a sterilization step (see FIG. 3, Step H). The particles 14 can be sterilized by a number of methods. For example, a preferred method is by irradiation, such as by gamma irradiation, which can further enhance the blood dissolution resistance, the tensile properties and the adhesion properties of the wound dressing. The irradiation can be conducted at a level of at least about 5 kGy, more preferably a least about 10 kGy, and most preferably at least about 15 kGy.

D. Altering the Properties of the Hemostatic Particles

The properties of the chitosan matrix 16 and thus of the particles 14 formed from it may be further optimized to provide for improved hemostatic performance to control non-compressible hemorrhage.

1. The Chitosan Salt Composition

For example, the composition of the chitosan salt can be optimized for promotion of rapid clotting. It has been discovered that chitosan with a high degree of deacetylation and high molecular weight more readily produces rapid clotting than chitosan with lower degree of deacetylation. It has also been discovered that salts of acetic, lactic and glycolic acids provide for this enhanced clot formation when certain levels of other adjuvants, e.g., iso-propyl alcohol, are present.

The local promotion of clotting can be augmented by adjusting the composition of the chitosan matrix 16 accordingly, e.g. by providing a range of high degree of deacetylation chitosan and high molecular weight matrices 16 of different density, of different acid (lactic, glycolic, acetic) with different concentrations of adjuvants such as iso-propyl alcohol. The matrices 16 can be granulated by a mechanical process, pouched, and sterilized prior to use in the manner previously described.

2. Homogeneous Mixing of the Chitosan Foam with Dense Chitosan Beads

Figure 4:
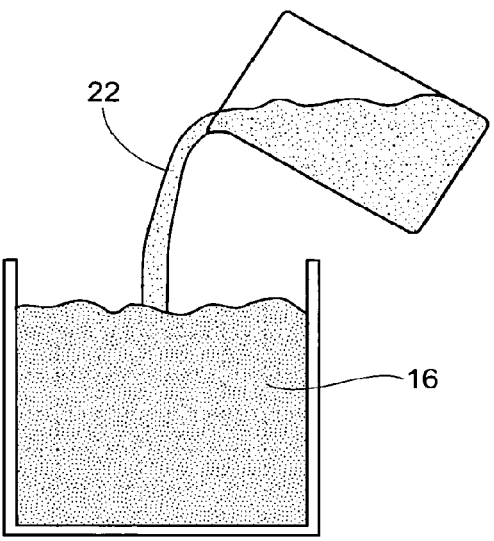
FIG. 4 shows an alternate step in the manufacturing process shown in FIG. 3, in which dense beads of chitosan material are added to the granules or particles.
Figure 5:
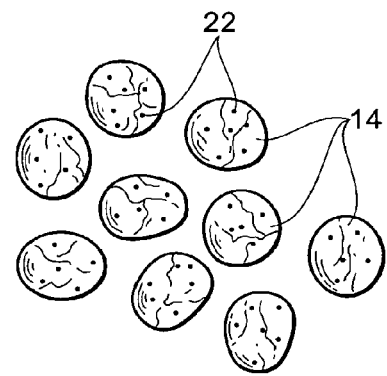
FIG. 5 shows a granule or particle that is formed that contains dense beads of chitosan material.

Chitosan beads 22 (shown in FIG. 4) of controlled diameter can be prepared by flow mixing of a chitosan acid solution and a polyanion solution (such as an alginate) across an oscillating electric field. After neutralization and drying, the beads 22 form small hard dense spheres that are relatively insoluble. As shown in FIG. 4, addition and homogeneous mixing of a significant fraction of these spherical beads 22 to a viscous chitosan solution 16 immediately prior to the freezing step (as above described) will result in a homogeneous dispersion of beads through the lyophilized foam sponge. In sufficient numbers these beads 22 will provide for a high density core in the center of the foam granulate particle 14, as FIG. 5 shows. The high density bead core formed by the beads 22 assists in more local application of the beaded particles 14 to a bleeding injury.

3. Mesh-Reinforced Particles

Figure 6:
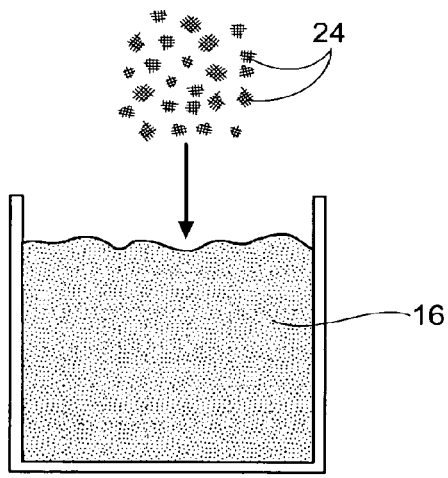
FIG. 6 shows an alternate step in the manufacturing process shown in FIG. 3, in which strips of a polymer mesh material are added to the granules or particles.
Figure 7:
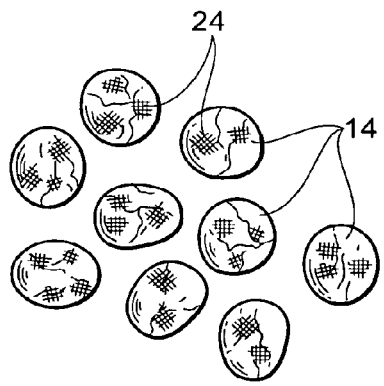
FIG. 7 shows a granule or particle that is formed that contains a polymer mesh material.
Figure 8:
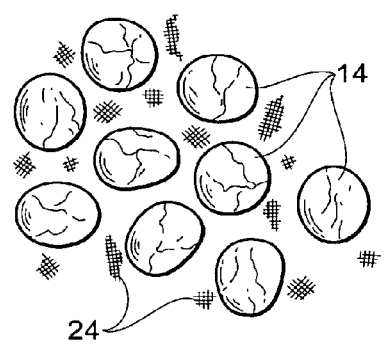
FIG. 8 shows a composite hemostatic agent comprising hemostatic granules or particles mixed with strips of polymer mesh material.

The interior of the particles 14 can be reinforced by the inclusion of small strips or pieces of a bioresorbable polymer mesh material 24 (as shown in FIGS. 6 and 7). These strips of mesh material 24 can be added to the viscous chitosan solution 16 immediately before the freezing step (as FIG. 6 shows). Alternatively (as FIG. 7 shows), loose small strips or pieces of a bioresorbable polymer mesh material 24 can be added after granulation and prior to pouching and sterilization. In this arrangement, the strips or pieces of mesh material 24 reside between the individual particles 14 contained within the pouch 22 (as shown in FIG. 8).

The presence of the mesh material 24 enhances hemostasis by overall reinforcement of the complex composite of chitosan granule particle 14, blood, and the mesh material 24.

The composition of the mesh material 24 can vary. It is believed that a mesh formed from poly-4-hydroxy butyrate (TephaFLEXX Material manufactured by Tepha Inc.) is desirable. This material is a biosynthetic absorbable polyester produced through a fermentation process rather than by chemical synthesis. It can generally be described as a strong, pliable thermoplastic with a tensile strength of 50 MPa, tensile modulus of 70 MPa, elongation to break of ~1000%, and hardness (Shore D) of 52.8. Upon orientation the tensile strength increases approximately 10-fold (to a value about 25% higher than commercial absorbable monofilament suture materials such as PDSII™).

Despite its biosynthesis route, the structure of the polyester is very simple, and closely resembles the structures of other existing synthetic absorbable biomaterials used in medical applications. The polymer belongs to a larger class of materials called polyhydroxyalkanoates (PHAs) that are produced in nature by numerous microorganisms. In nature these polyesters are produced as storage granules inside cells, and serve to regulate energy metabolism. They are also of commercial interest because of their thermoplastic properties, and relative ease of production. Tepha, Inc. produces the TephaFLEXTh biomaterial for medical applications using a proprietary transgenic fermentation process specifically engineered to produce this homopolymer. The TephaFT.F.X™ hiomateria] production process utilizes a genetically engineered *Escherichia coli* K12 microorganism that incorporates new biosynthetic pathways to produce the polymer. The polymer accumulates inside the fermented cells during fermentation as distinct granules, and can then be extracted at the end of the process in a highly pure form. The biomaterial has passed tests for the following: cytotoxicity; sensitization; irritation and intracutaneous reactivity; hemocompatibility; endotoxin; implantation (subcutaneous and intramuscular); and USP Class VI. In vivo, the TephaFLEX™ biomaterial is hydrolyzed to 4-hydroxybutyrate, a natural human metabolite, present normally in the brain, heart, lung, liver, kidney, and muscle. This metabolite has a half-life of just 35 minutes, and is rapidly eliminated from the body (via the Krebs cycle) primarily as expired carbon dioxide.

Being thermoplastic, the TephaFLEX™ biopolymer can be converted into a wide variety of fabricated forms using traditional plastics processing technologies, such as injection molding or extrusion. Melt extruded fibers made from this novel absorbable polymer are at least 30% stronger, significantly more flexible and retain their strength longer than the commercially available absorbable monofilament suture materials. These properties make the TephaFLEX™ biopolymer an excellent choice for construction of a hemostatic dressing for controlling intracavity hemorrhage.

The TephaFLEXTh biomaterial can be processed into fibers and fabrics suitable for use as an absorbable sponge.

E. Delivery of the Particles

To provide for enhanced local delivery and potentially some pressure compaction (tamponade) of the encased granulate against the wound, the chitosan granulate particles 14 can be desirable housed for delivery within an open mesh socklet or bag 26 (see FIG. 9) The socket 26 can be made, e.g., from a TephaFLEX biomaterial above described.

The mesh of the socklet 26 is sufficiently open to allow for the chitosan granulate particles 14 to protrude out of the socklet 26, but not so open that granulate particles 14 could be flushed away by flowing blood through the mesh. The socklet 26 supports the chitosan granulate particles 14 during and after delivery and allows a more directed application of a bolus of the granulate particles 14. The mesh socklet 26 should be sufficiently open to allow protrusion of chitosan particles 14 at the outer surface of the bolus from its outside surface without loss of individual chitosan granule particles 14. The mechanical properties of the mesh socklet 26 are sufficient to allow local application of pressure over its surface without tearing or breaking.

Figure 10:
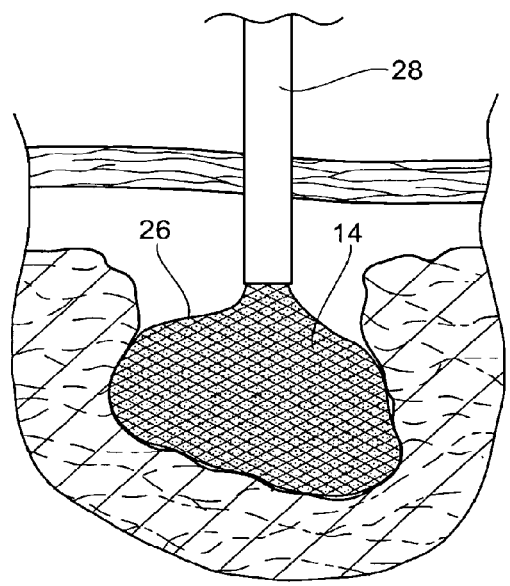
FIG. 10 shows one way of delivering the bolus of the granules or particles shown in FIG. 9 in the socklet of polymer mesh material to an injury site.

The tamponade of a socklet 26 filled with the particles 14 can be applied, e.g., through a cannula 28 (see FIG. 10) by use of tamp 34 to advance the socklet 26 through the cannula 28 to the injury site 10. Multiple socklets 26 can be delivered in sequence through the cannula 28, if required. Alternatively, a caregiver can manually insert one or more of the socklets 26 into the treatment site 10 through a surface incision.

Figure 9:
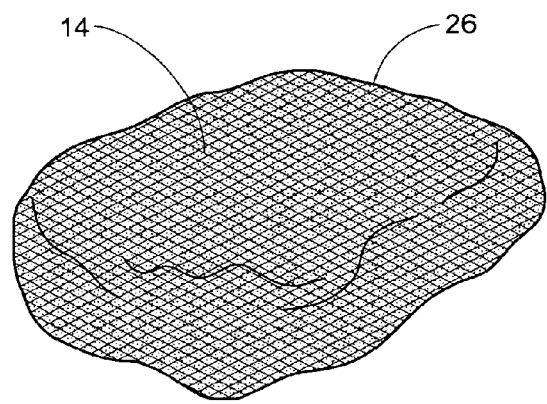
FIG. 9 shows a bolus of the granules or particles shown in FIG. 2 or 4 or 7 contained for delivery in a socklet of polymer mesh material.
Figure 11A:
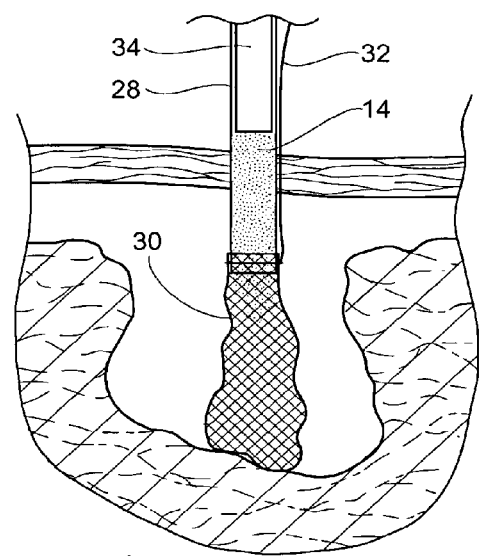
FIGS. 11A and 11B show a way of delivering a bolus of the granules or particles shown in FIG. 2 or 4 or 7 into a releasable polymer mesh socklet at an injury site.
Figure 11B:
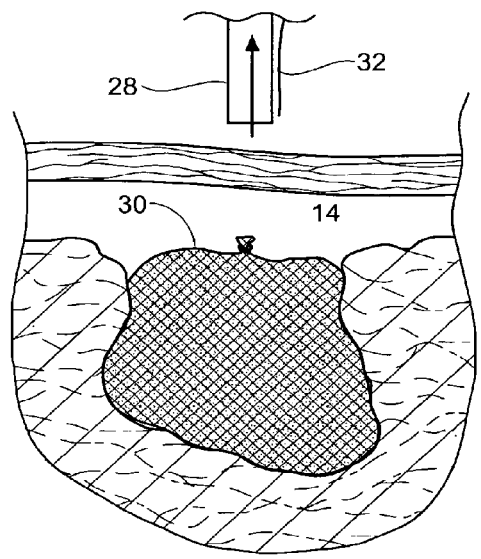

Alternatively, as FIGS. 11A and 11B show, a mesh socklet 30 can be releasably attached to the end of a cannula 28, e.g., by a releasable suture 32. The cannula 28 guides the empty socklet 30 into the injury site 10. In this arrangement, individual particles 14 (i.e., not confined during delivery within a mesh socklet 26 as shown in FIG. 9) can be urged through the cannula 28, using, e.g., a tamp, to fill the socklet 30 within the injury site. Upon filling the socklet 30 with particles 14, the suture 32 can be pulled to release the cannula 28, leaving the particle filled socklet 30 behind in the injury site 10, as FIG. 11B shows.

Figure 12:
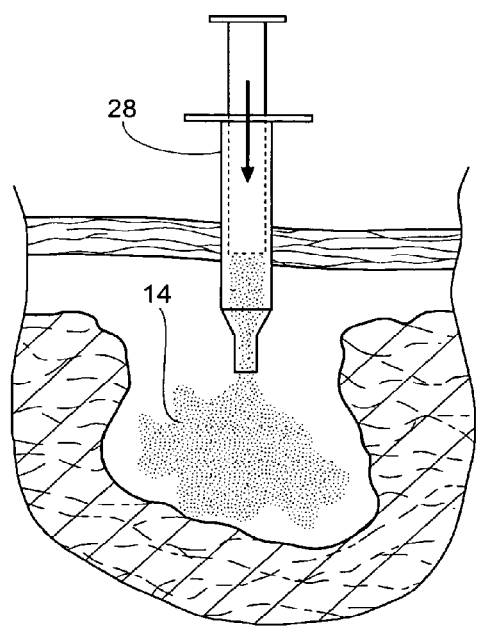

Alternatively, as FIG. 12 shows, individual particles 14 can be delivered to the injury site 10 through a syringe 36. In this arrangement, means for targeting of the particles 14 at the injury site 10 and protection against disbursement of the particles 14 away from the injury site 10 due to blood flow may be required, using the already described confinement devices and techniques. It is believed that permanent internal use will require the use of a socklet or equivalent confinement technique.

II. GRANULAR HEMOSTATIC AGENT

Another Embodiment

Granular chitosan salt and potentially granular chitin by itself or in combination with inorganic calcium would be a very useful hemostatic agent for rapid delivery to superficial and difficult to access bleeding sites. Such granules, if prepared from suitable purified stock, would also be able to be used without concern for immunological, inflammatory, cytotoxic or thermal injury effects (due to control of hemostasis by producing heat).

An effective hemostatic particulate (granular) chitosan foam has been previously described. In an alternative embodiment, as will now be described, an equally effective granular hemostatic form (i.e., comprising another representative form of the particle 14 as previously described) can be created with minimal processing, almost directly from a chitosan source supply. In this embodiment, no lyophilization or other foam forming procedure is necessary. The granular hemostatic material in this embodiment is obtained from controlled grinding (to controlled particle size) of deproteinized and potentially decalcified (or potentially fully decalcified) crustacean shell material, which is then partially (30%) or near fully (80-85%) deacetylated.

Deproteinized and decalcified crustacean exoskeleton is most generally referred to as "chitin" or $\text{poly}\beta\text{-}(1\rightarrow4)$w-acetyl-D-glucosamine or $\text{poly}\beta\text{-}(1\rightarrow4)$2-acetamide-2-D-glucopyranose. The correct nomenclature (RUPAC) is $\text{poly}[\beta\text{-}(1\rightarrow4)\text{-}2\text{-acetimide-2-deoxy-D-glucopyranose}$, however for convenience we will call this material (deacetylized, to at most 30%) chitin.

The chitin shell material can be obtained, e.g., from squid, crabs, or other crustacean. The chitin granule, as ground to form the particle 14, may be used to control hemorrhage and to act as a hemostatic agent in all the manners and embodiments previously described.

To enhance the surface area of the chitin granule, it may be expanded and partially ruptured by rapid release under vacuum of an absorbed, volatile swelling agent. Such partially ruptured and expanded particles, beads or granules 14 of chitin could be achieved by rapid release of pressure heating in particles containing a high fraction of absorbed $CO_2$ or other volatile solvent. The extent of rupturing of the particle may be controlled by the uniformity and depth of absorption of the volatile swelling agent in the particle or granule.

Controlled rupturing of particle surface and bulk results in the preparation of granules 14 with controlled surface and bulk properties. Freezing of absorbed solvent (one which experiences an increase in specific volume or freezing) would be another method for controlled rupturing.

As an example, a particle 14 which is prepared with about two-thirds of the interior of the particle radius intact (not expanded) and about the other one-third of particle radius expanded at the surface enables a dense particle core and a significantly less dense, high specific surface area particle surface. The high specific area surface provides for enhanced hemostatic interaction with blood, while the dense core provides for sufficient particle density to overcome buoyancy and other fluid flow related delivery problems.

Enhanced density can also be achieved by the addition of iron and/or calcium to the expanded particle. Enhanced density leads to enhanced hemostasis.

Chitin or expanded chitin particles 14 may be further processed to chitosan by enzymatic or hydrolytic treatment. Chitosan is generally chitin that has been deacetylated to more than 50% degree of deacetylation. Although it generally does contain residual acetyl groups which are present in block or random repeat units along the polymer chain, chitosan is often referred to as $\text{poly}\beta\text{P-}(1\rightarrow4)$D-glucosamine or more correctly (RUPAC) $\text{poly}\beta\text{-}(1\rightarrow4)$. w-acetyl-D-glucosamine or $\text{poly}\beta\text{-}(1\rightarrow4)$2-amino-2-deoxy-D-glucopyranose.

Because all commercial deacetylation of chitin is done heterogeneously (particles dispersed in a deacetylation medium) it is possible to prepare particles with a non-uniform degree of deacetylation. Such non-uniformity would present itself as a higher degree of deacetylation at the particle surface compared to the particle core. Granules, particles or beads with higher degree of deacetylation at the surface compared to the bulk is advantageous in preparation of highly efficacious hemostatic chitosan/chitin granules since addition of acetic acid to the granular surface or other types of acid such as lactic, glycolic hydrochloric, glutamic, propionic, citric or other mono-acids, di-acids or tri-acids provides for catonic and muco-adhesive properties that promote erythrocyte agglutination and enhanced hemostasis. The advantage of surface localized muco-adhesive properties ensures that the reactive groups are located where they will most effectively interact with blood and also the core of the particle is not muco-adhesive, meaning that it is insoluble in blood and will provide a dense chitin center for extended efficacy of the particle, for its effective delivery and for enhanced agglomeration of blood and other particles of similar structure to form a strong and adhesive clot.

Another advantage of localization of the deacetylated chitin (chitosan) at the particle surface, especially in the case of ruptured/expanded bead or granule is that derivatization of the chitosan amine groups is then readily possible to create a high specific surface area functionalized bead/granule/particle that could be used effectively for hemostasis, antibacterial or antiviral application.

III. CONCLUSION

It should be apparent that above-described embodiments of this invention are merely descriptive of its principles and are not to be limited. The scope of this invention instead shall be determined from the scope of the following claims, including their equivalents.

The invention claimed is:

1. A hemostatic chitosan material in granule or particle form having a density between about 0.25 to 0.60 g/cm$^3$ and a granule or particle diameter of about 0.9 mm, wherein said granules or particles are produced by freeze-drying a frozen matrix of chitosan, heat-compressing said matrix, and then granulating the compressed matrix.

2. The hemostatic chitosan material of claim 1, wherein the at least one of the granules or particles includes dense chitosan beads.

3. The hemostatic chitosan material of claim 1, wherein the density of the hemostatic chitosan material in the form of a granule or particle is between about 0.25 to 0.50 g/cm3.

4. The hemostatic chitosan material of claim 1, further comprising a chitosan salt.

5. The hemostatic chitosan material of claim 4, wherein the chitosan salt is selected from the group consisting of chitosan acetate, chitosan lactate, and chitosan hydroxyacetate.

6. A hemostatic device comprising a mesh socklet and the hemostatic chitosan material of claim 1.

7. The hemostatic device of claim 6, wherein the device further comprises strips of a polymer mesh material.

8. The hemostatic device of claim 6, wherein the mesh socklet comprises a polymer material.

9. The hemostatic device of claim 6, wherein the mesh socklet comprises openings sized to allow for the granules or particles to protrude out of the mesh socklet.

10. The hemostatic device of claim 6, wherein the density of the chitosan material in the form of a granule or particle is between about 0.25 to 0.50 g/cm3.

11. The hemostatic device of claim 6, wherein the chitosan material comprises a chitosan salt.

12. The hemostatic device of claim 11, wherein the chitosan salt is selected from the group consisting of chitosan acetate, chitosan lactate, and chitosan hydroxyacetate.

13. The hemostatic device of claim 6, further comprising a cannula.

14. The hemostatic device of claim 6, further comprising a syringe.

15. A hemostatic agent comprising chitosan or chitin crustacean shell material which has been at least partially or fully deproteinized, and partially or fully deacetylized, wherein the chitosan or crustacean shell material is ground into granule or particle form, and wherein the chitosan or chitin granules or particles are expanded and partially ruptured such that about two-thirds of an interior of a granule or particle radius is intact and about a remaining one-third of the granule or particle radius is expanded at the surface of said granule or particle.

16. The hemostatic agent of claim 15, wherein the granule or particle form is fully deproteinized and partially or fully deacetylized chitosan material.

17. The hemostatic agent of claim 16, wherein the chitosan material comprises a chitosan salt.

18. The hemostatic agent of claim 17, wherein the chitosan salt is selected from the group consisting of chitosan acetate, chitosan lactate, and chitosan hydroxyacetate.

* * * * *